(12) United States Patent
Yang et al.

(10) Patent No.: US 8,686,179 B2
(45) Date of Patent: Apr. 1, 2014

(54) FLUORINATED AROMATIC BIS(ACYL)-CONTAINING COMPOUNDS AND POLYESTERS PREPARED THEREFROM

(75) Inventors: Yu Yang, Eden Prairie, MN (US); Lei Wang, San Jose, CA (US); George G. I. Moore, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 283 days.

(21) Appl. No.: 13/322,217

(22) PCT Filed: Jun. 7, 2010

(86) PCT No.: PCT/US2010/037607
§ 371 (c)(1),
(2), (4) Date: Nov. 23, 2011

(87) PCT Pub. No.: WO2011/005396
PCT Pub. Date: Jan. 13, 2011

(65) Prior Publication Data
US 2012/0071626 A1    Mar. 22, 2012

Related U.S. Application Data

(60) Provisional application No. 61/186,448, filed on Jun. 12, 2009, provisional application No. 61/289,060, filed on Dec. 22, 2009.

(51) Int. Cl.
C07C 303/00    (2006.01)

(52) U.S. Cl.
USPC .......................................................... 560/12

(58) Field of Classification Search
USPC ................ 528/290; 564/97; 568/661; 560/12
See application file for complete search history.

(56) References Cited

U.S. PATENT DOCUMENTS

| | | | |
|---|---|---|---|
| 3,663,708 A | 5/1972 | Harrington |
| 3,787,351 A | 1/1974 | Olson |
| 6,197,426 B1 | 3/2001 | Coppens |
| 6,664,354 B2 | 12/2003 | Savu |
| 6,726,966 B2 | 4/2004 | Negoro |
| 6,753,380 B2 | 6/2004 | Qiu |
| 6,852,781 B2 | 2/2005 | Savu |
| 7,199,197 B2 | 4/2007 | Caldwell |
| 7,361,782 B2 | 4/2008 | Klun |
| 2003/0001130 A1 | 1/2003 | Qiu |
| 2003/0139549 A1 | 7/2003 | Savu |
| 2007/0276065 A1 | 11/2007 | Barton |
| 2008/0306238 A1 | 12/2008 | Jariwala |
| 2010/0227148 A1 | 9/2010 | Jariwala |

FOREIGN PATENT DOCUMENTS

| | | |
|---|---|---|
| DE | 2107914 | 2/1971 |
| GB | 1497618 | 1/1978 |
| WO | WO 02/072537 | 9/2002 |
| WO | WO 2008/154421 | 12/2008 |

OTHER PUBLICATIONS

Lindsley et al. (Design, synthesis, and SAR of macrocyclic tertiary carbinamine BACE-1 inhibitors, Bioorganic & Medicinal Chemistry Letters, vol. 17, pp. 4057-4061, 2007, IDS filed Aug. 2, 2012).*
Garvie, "Phase Analysis in Zirconia Systems", Journal of the American Ceramic Society, Jun. 1972, vol. 55, No. 6, pp. 303-305.
Kim, "Lattice Parameters, Ionic Conductivities, and Solubility Limits in Fluorite-Structure $MO_2$ Oxide ($M = Hf^{4+}, Zr^{4+}, Ce^{4+}, Th^{4+}, U^{4+}$) Solid Solutions", Journal of the American Ceramic Society, Aug. 1989, vol. 72, No. 8, pp. 1415-1421.
Kitano, "Structural Changes by Mechanical and Thermal Stresses of 2.5-mol%-$Y_2O_3$—Stabilized Tetragonal $ZrO_2$ Polycrystals", Journal of the American Ceramic Society, Aug. 1988, vol. 71, No. 8, pp. C382-C383.
Lindsley, "Design, synthesis, and SAR of macrocyclic tertiary carbinamine BACE-1 inhibitors", Bioorganic & Medicinal Chemistry Letters, Jul. 15, 2007, vol. 17, No. 14, pp. 4057-4061.
Tsuwi, "Molecular dynamics in semifluorinated side-chain polyesters as studied by broadband dielectric spectroscopy", Polymer, Sep. 20, 2006, vol. 47, No. 20, pp. 7189-7197.
International Search Report for PCT/US2010/037607, 7 pages.

* cited by examiner

Primary Examiner — Wu-Cheng Winston Shen
Assistant Examiner — Blaine G Doletski
(74) Attorney, Agent, or Firm — Jean A. Lown

(57) ABSTRACT

A fluorinated bis(acyl)-containing compound of Formula (I), where $R^1$, Ar, L, $R^2$, $R^3$, Rf, n, p and q are as defined in the claims, and a fluorinated polyester formed from the fluorinated bis(acyl) compound are described. More particularly, the fluorinated bis(acyl) has an aromatic ring bonded to two acyl groups plus at least one third group that contains a perfluoroalkylsulfonamido group. The fluorinated polyesters formed from the fluorinated bis(acyl)-containing compound can be used to provide a low energy surface with a relatively low refractive index compared to many other polyesters. A method of preparing a monosubstituted-arylene compound of formula $Rf^1$-$L^2$-$CH_2$—$Ar^2$—$CH_2$—W, where $Ar^2$, $Rf^1$, $L^2$, $R^6$ and W are as defined in the claims by reaction of a compound of formula $Rf^1$-$L^2$-H with a compound of formula W—$CH_2$—$Ar^2$—$CH_2$—W.

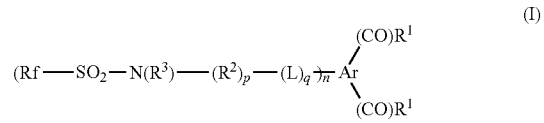

10 Claims, No Drawings

FLUORINATED AROMATIC BIS(ACYL)-CONTAINING COMPOUNDS AND POLYESTERS PREPARED THEREFROM

CROSS REFERENCE TO RELATED APPLICATIONS

This application is a national stage filing under 35 U.S.C. 371 of PCT/US2010/037607, filed Jun. 7, 2010, which claims priority to U.S. Provisional Application No. 61/186,448, filed Jun. 12, 2009, and U.S. Provisional Application No. 61/289,060, filed Dec. 22, 2009, the disclosure of which is incorporated by reference in its/their entirety herein.

TECHNICAL FIELD

Fluorinated aromatic bis(acyl)-containing compounds and polyesters prepared from the fluorinated aromatic bis(acyl)-containing compounds are described.

BACKGROUND

Fluorinated polymeric materials have been prepared previously that can be used in applications where enhanced oil and water repellency are desirable. Some of these fluorinated polymeric materials have included perfluorooctyl groups. Certain perfluorooctyl-containing compounds tend to bioaccumulate in living organisms. This tendency has been cited as a potential concern regarding some fluorochemical materials. New fluorochemical materials that can be effectively eliminated from the body and that provide effective water and oil repellency are desired.

SUMMARY

Fluorinated and aromatic bis(acyl)-containing compounds and fluorinated polyesters prepared from the bis(acyl)-containing compounds are described. More particularly, the bis(acyl)-containing compound has an aromatic ring and contains a perfluoroalkylsulfonamido group. The fluorinated polyesters that are prepared from the bis(acyl)-containing compounds can be used to provide a low energy surface with a relatively low refractive index compared to many other known polyesters.

In one aspect a compound of Formula (I) is provided.

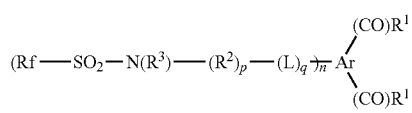

(I)

In Formula (I), each $R^1$ is independently a halo, hydroxyl, alkoxy, or aryloxy, wherein the alkoxy is unsubstituted or substituted with an aryl and the aryloxy is unsubstituted or substituted with a halo, alkyl, or a combination thereof. The group Ar is a carbocyclic aromatic ring structure having at least 6 carbon atoms. The group L is oxy, thio, or sulfonyl. The group $R^2$ is a divalent group selected from an alkylene, heteroalkylene, arylene, or a combination thereof The group $R^3$ is an alkyl and the group Rf is a perfluoroalkyl. The variable n is equal to an integer in the range of 1 to 4. The variable p and q can each be equal to zero or one with the proviso that if p is equal to zero, then q is equal to zero.

In another aspect, a fluorinated polyester is provided that is a condensation reaction product of a plurality of monomers that include (a) a compound of Formula (I) as described above and (b) a diol.

In yet another aspect, a fluorinated polyester is provided that is a condensation reaction product of a plurality of monomers that include (a) a compound of Formula (I) as described above, (b) a diol, and (c) a mono-functional end capping compound that is reactive with the compound of Formula (I) or with the diol.

In a still further aspect, compounds of Formula (II) are provided.

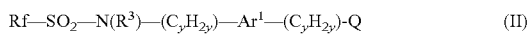

In Formula (II), Rf is a perfluoroalkyl, $R^3$ is an alkyl, y is an integer in the range of 1 to 20, $Ar^1$ is phenylene or diphenylene, and Q is selected from a halo or group of formula $—OSO_2—R^4$ where $R^4$ is an alkyl, perfluoroalkyl, aryl, or aryl substituted with an alkyl.

Another aspect of the invention is a method of preparing a monosubstituted-arylene compound of Formula (XV) $Rf^1-L^2-CH_2—Ar^2—CH_2—W$, wherein: $Ar^2$ is a phenylene or diphenylene; $Rf^1$ is a perfluoroalkyl with optional O or N within the chain; $L^2$ is selected from $—O—$, $—SO_2—$, $—CH_2—O—$, $—C_2H_4—O—$, $—C_2H_4—S—$, and $—SO_2—N(R^6)—$; $R^6$ is a C1-C4 alkyl; and W is a leaving group. The method includes combining a base with components comprising: a compound of Formula (XVI) $Rf^1-L^2-H$, a compound of Formula (XVII) $W—CH_2—Ar^2—CH_2—W$, and an organic solvent, over a period of time effective to form the monosubstituted-arylene compound of Formula (XV), wherein: $Rf^1$ is a perfluoroalkyl with optional O or N within the chain; $L^2$ is selected from $—O—$, $—SO_2—$, $—CH_2—O—$, $—C_2H_4—O—$, $—C_2H_4—S—$, and $—SO_2—N(R^6)—$ wherein $R^6$ is a C1-C4 alkyl; $Ar^2$ is a phenylene or diphenylene; and W is a leaving group.

The above summary of the present invention is not intended to describe each embodiment or every implementation of the present invention. The Figures, Detailed Description, and Examples that follow more particularly exemplify these embodiments.

DETAILED DESCRIPTION OF THE INVENTION

A fluorinated and aromatic bis(acyl)-containing compound and a fluorinated polyester formed from the fluorinated aromatic bis(acyl)-containing compound are described.

The terms "a", "an", and "the" are used interchangeably with "at least one" to mean one or more of the elements being described.

The term "alkyl" refers to a monovalent group that is a radical of an alkane and includes groups that are linear, branched, cyclic, or combinations thereof. The alkyl group typically has 1 to 30 carbon atoms. In some embodiments, the alkyl group contains 1 to 20 carbon atoms, 1 to 10 carbon atoms, 1 to 6 carbon atoms, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "alkylene" refers to a divalent group that is a radical of an alkane. The alkylene can be straight-chained, branched, cyclic, or combinations thereof. The alkylene typically has 1 to 30 carbon atoms. In some embodiments, the alkylene contains 1 to 20, 1 to 10, 1 to 6, or 1 to 4 carbon atoms. The radical centers of the alkylene can be on the same carbon atom (i.e., an alkylidene) or on different carbon atoms.

The term "alkoxy" refers to a monovalent group of formula —OR where R is an alkyl group.

The term "aromatic bis(acyl)" refers to a group of formula —(CO)—Ar—(CO)—. The group Ar is a carbocyclic aromatic ring having at least 6 carbon atoms. The two carbonyl groups are attached to directly to the aromatic ring. Each carbonyl group is further bonded to another group such as, for example, a halo, alkoxy, aryloxy, or hydroxyl. That is, compounds that contain the aromatic bis(acyl) group are often aromatic bis(acyl halides), aromatic bis(esters), or aromatic bis(carboxylic acids). Aromatic bis(acyl halides) have two groups of formula —(CO)X attached to the group Ar. The group X is typically a halo selected from bromo, chloro, iodo, or fluoro. Aromatic bis(esters) have two groups of formula —(CO)OR$^a$ attached to the Ar group. The group R$^a$ is an alkyl, alkyl substituted with an aryl, aryl, aryl substituted with a halo, alkyl, or a combination thereof Aromatic bis(carboxylic acids) have two groups —(CO)OH or salts thereof attached to the group Ar.

The term "aryl" refers to a monovalent group that is aromatic and carbocyclic. The aryl can have one to five rings that are connected to or fused to the aromatic ring. The other ring structures can be aromatic, non-aromatic, or combinations thereof Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "aryloxy" refers to a group of formula —O—Ar$^1$ where Ar$^1$ is an aryl.

The term "(CO)" or "(OC)" are used interchangeably to refer to a carbonyl group.

The term "halo" refers to fluoro, chloro, bromo, or iodo.

The term "heteroalkylene" refers to a divalent alkylene having one or more —CH$_2$— groups replaced with a thio, oxy, or —NR$^b$— where R$^b$ is hydrogen or alkyl. The heteroalkylene can be linear, branched, cyclic, or combinations thereof and can include up to 60 carbon atoms and up to 15 heteroatoms. In some embodiments, the heteroalkylene includes up to 50 carbon atoms, up to 40 carbon atoms, up to 30 carbon atoms, up to 20 carbon atoms, or up to 10 carbon atoms.

The term "perfluoroalkyl" refers to an alkyl in which all of the hydrogen atoms are replaced with a fluorine atom.

The term "oxy" refers to the divalent group —O—.

The term "sulfonyl" refers to the divalent group —SO$_2$—.

The term "thio" refers to the divalent group —S—.

The term "in the range" includes the endpoints of the stated range.

A fluorinated aromatic bis(acyl)-containing compound of Formula (I) is provided.

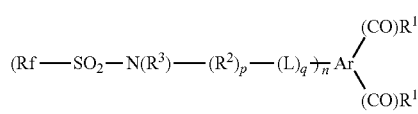
(I)

The Ar group in this formula is a carbocyclic aromatic ring structure having at least 6 carbon atoms. Each R$^1$ in Formula (I) is independently a halo, hydroxyl, alkoxy, or aryloxy, wherein the alkoxy is unsubstituted or substituted with an aryl and the aryloxy is unsubstituted or substituted with an alkyl, halo, or combination thereof. The group L is oxy, thio, or sulfonyl. The group R$^2$ is a divalent group selected from an alkylene, heteroalkylene, arylene, or a combination thereof. The group R$^3$ is an alkyl and the group Rf is a perfluoroalkyl. The variable n is equal to an integer in the range of 1 to 4 and the variable p and q can each be equal to zero or one with the proviso that if p is equal to zero, then q is equal to zero. That is, L is not bonded directly to —N(R$^3$)— in formula (I).

In some embodiments of Formula (I), both p and q are equal to one as shown in Formula (Ia)

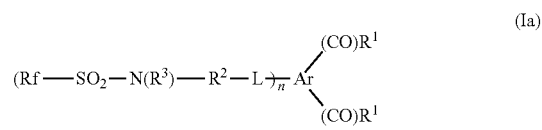
(Ia)

and the perfluoroalkylsulfonamido group is separated from the aromatic ring structure by the divalent group —R$^2$-L-. In other embodiments, both p and q are equal to zero as shown in Formula (Ib)

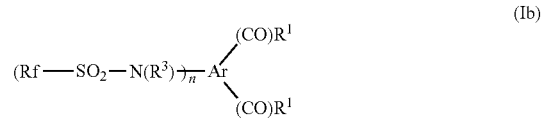
(Ib)

and the perfluoralkylsulfonamido group is attached directly to the aromatic ring Ar. In still other embodiments, p is equal to 1 and q is equal to zero as shown in Formula (Ic)

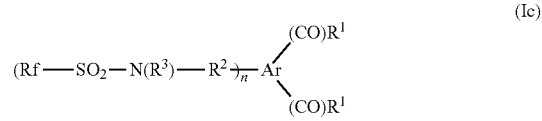
(Ic)

and the perfluoroalkylsulfonamido group is separated from the aromatic ring structure by the divalent group —R$^2$—.

The Ar group in Formula (I) is often a single carbocyclic aromatic ring (i.e., the Ar group is a benzene ring). Alternatively, the Ar group can include two or more aromatic rings that are fused (e.g., naphthalene) or connected by a single bond (e.g. biphenyl). When the Ar group includes multiple aromatic rings, the at least three groups connected to the Ar group in Formula (I) can all be attached to the same aromatic ring, or the at least three groups can be distributed in any suitable configuration on multiple aromatic rings.

Each R$^1$ group in Formula (I) is independently a halo, hydroxyl, alkoxy, or aryloxy. Often, both R$^1$ groups are the same. Suitable halo groups include chloro, bromo, and iodo. Suitable alkoxy R$^1$ groups often have 1 to 10 carbon atoms, 1 to 8 carbon atoms, 1 to 6 carbon atoms, or 1 to 4 carbon atoms. Any alkoxy group can be further substituted with an aryl group such as, for example, a phenyl group or a biphenyl group. Suitable aryloxy groups often have a single aromatic ring (i.e., the aryloxy group is a phenoxy) or two or more aromatic rings connected with a single bond. The aryloxy group can be further substituted with a halo or with an alkyl group such as an alkyl group having 1 to 10 carbon atoms, 1 to 8 carbon atoms, 1 to 6 carbon atoms, or 1 to 4 carbon atoms.

The group $R^2$ is included in Formula (I) when p is equal to 1. If present, the $R^2$ group can be a divalent group selected from an alkylene, heteroalkylene, arylene, or a combination thereof. Suitable alkylene groups often have 1 to 20 carbon atoms, 1 to 16 carbon atoms, 1 to 12 carbon atoms, 1 to 10 carbon atoms, 1 to 8 carbon atoms, 1 to 6 carbon atoms, or 1 to 4 carbon atoms. Suitable heteroalkylene groups often have an oxygen heteroatom and include 2 to 20, 2 to 16, 2 to 12, 2 to 8, or 2 to 4 carbon atoms. Suitable arylene groups often have one or two aromatic rings. Exemplary arylene groups include, but are not limited to, phenylene and biphenylene. Any combinations of these groups can be present.

In some exemplary compounds of Formula (I), the group $R^2$ is an alkylene. That is, the group $R^2$ can be a divalent group of formula —$(C_yH_{2y})$— where y is equal to an integer in the range of 1 to 20, in the range of 1 to 12, in the range of 1 to 8, or in the range of 1 to 4.

In other exemplary compounds of Formula (I), the group $R^2$ is a combination of one or more arylene groups and one or more alkylene groups. For example, a first alkylene can be bonded to an arylene and the arylene can be further bonded to a second arylene. That is, $R^2$ is of the formula —$(C_yH_{2y})$—$Ar^1$—$(C_yH_{2y})$— where $Ar^1$ is an arylene and each variable y is an integer in the range of 1 to 20, in the range of 1 to 12, in the range of 1 to 8, or in the range of 1 to 4. The group $Ar^1$ typically includes 1 to 3 aromatic rings that are fused or linked together with a single bond. Some examples include, but are not limited to, a group of formula —$(C_yH_{2y})$—$C_6H_4$—$(C_yH_{2y})$— such as —$CH_2$—$C_6H_4$—$CH_2$— or a group of formula —$(C_yH_{2y})$—$C_6H_4$—$C_6H_4$—$(C_yH_{2y})$— such as —$CH_2$—$C_6H_4$—$C_6H_4$—$CH_2$—.

Group $R^3$ in Formula (I) is an alkyl. Suitable alkyl groups often have 1 to 18 carbon atoms, 1 to 12 carbon atoms, 1 to 8 carbon atoms, or 1 to 4 carbon atoms. In many embodiments, $R^3$ is methyl.

Group Rf is a perfluoroalkyl. Suitable perfluoroalkyl often have 1 to 20 carbon atoms, 1 to 10 carbon atoms, 1 to 8 carbon atoms, 1 to 6 carbon atoms, or 1 to 4 carbon atoms. In many embodiment, the group Rf is —$C_4F_9$, —$C_6F_{13}$, or —$C_8F_{17}$. More particularly, the Rf group is often n-perfluorobutyl (i.e., a linear —$C_4F_9$ group).

Some exemplary compounds of Formula (I) are of Formula (Id) or (Ie).

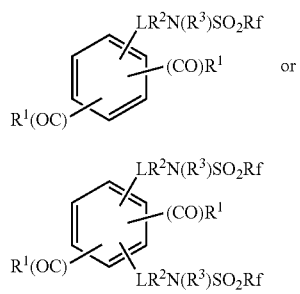

In these formulas, the group Ar in Formula (I) is a benzene ring. The groups L, $R^1$, $R^2$, and Rf are the same as defined above for Formula (I). The variable n of Formula (I) is equal to 1 in Formula (Id) and equal to 2 in Formula (Ie). The variables p and q in Formula (I) are both equal to 1 in Formulas (Id) and (Ie). In Formulas (Id) and (Ie), the groups —(CO) $R^1$ and -L$R^2$N(CH$_3$)SO$_2$Rf can be bonded to any of the carbon atoms of the benzene ring.

In some embodiments of Formula (Id) or (Ie), $R^2$ is an alkylene as shown in Formulas (If) and (Ig) where $R^2$ is equal to the divalent group —$(C_yH_{2y})$— where y is the same as defined above.

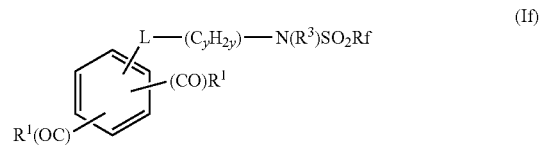

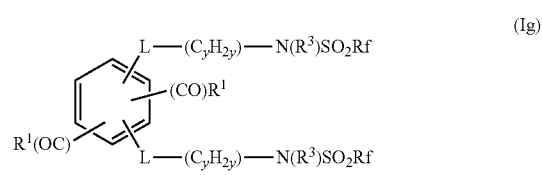

Exemplary compounds of Formula (If) include, but are not limited to,

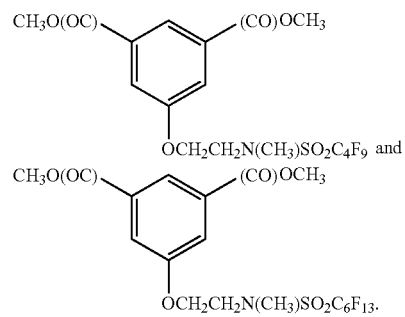

Exemplary compound of Formula (Ig) include, but are not limited to,

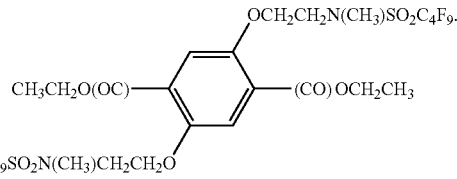

In other embodiments of Formula (Id), $R^2$ is equal to the divalent group —$(C_yH_{2y})$—$Ar^1$—$(C_yH_{2y})$— as shown in Formulas (Ih) where $Ar^1$ is phenylene or diphenylene and y is the same as define above.

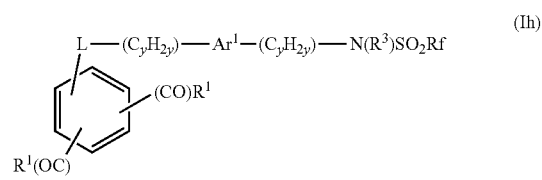

Exemplary compounds of Formula (Ih) include, but are not limited to,

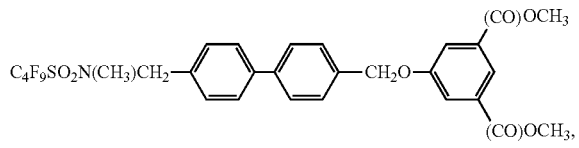

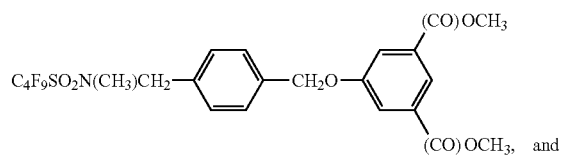

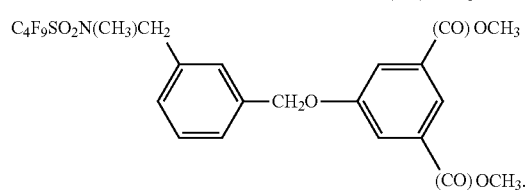

In still other exemplary compound of Formula I(d), $R^2$ is equal to the divalent group —$Ar^1$—$(C_yH_{2y})$— as shown in Formulas (Ii) where $Ar^1$ is phenylene or diphenylene and y is the same as defined above.

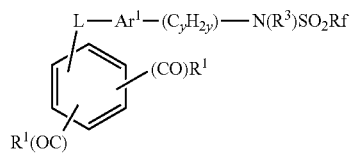
(Ii)

Specific compound of Formula (Ii) include, but are not limited to,

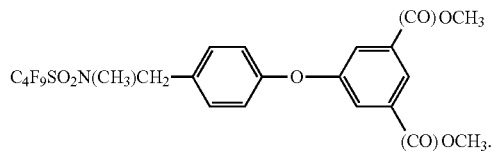

In other embodiments of Formula (I), the variable p and q are both equal to zero as shown in Formula (Ib) above. In these embodiments, the compounds are often of Formula Ij).

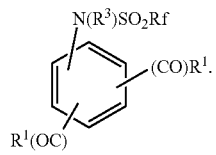
(Ij)

Exemplary compounds of Formula (Ij) include, but are not limited to,

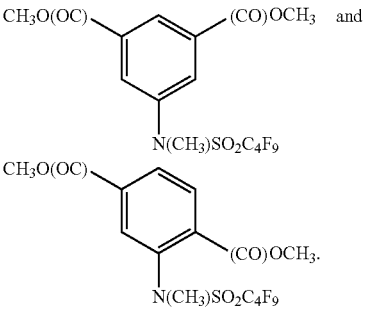
and

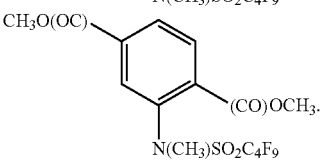

In still other embodiments of Formula (I), the variable p is equal to 1 but the variable q is equal to zero as shown in Formula (Ic) above. In these embodiments, the compounds are often of Formula (Ik).

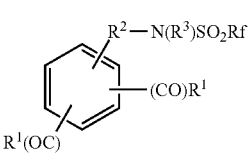
(Ik)

In many compounds of this formula, $R^2$ is an alkylene of formula —$(C_yH_{2y})$— as shown in Formula (Il) where y is the same as defined above.

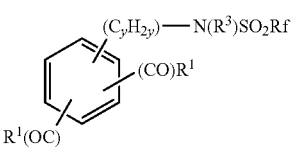
(Il)

Exemplary compounds of Formula (Il) include, but are not limited to,

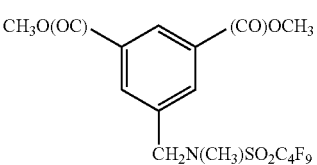

The compound of Formula (I) can be prepared by any suitable process. In many embodiments, the variables p and q are both equal to one and the compound can be prepared using Reaction Scheme A.

Reaction Scheme A

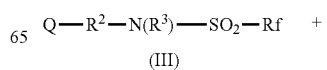
(III)

-continued

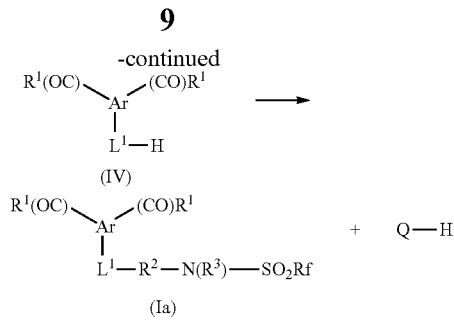

In this reaction scheme, a perfluoroalkylsulfonamido compound of Formula (III) is reacted with the aromatic bis(acyl) precursor of Formula (IV) to prepare the fluorinated and aromatic bis(acyl)-containing compound of Formula (Ia). In these various formulas, the group $L^1$ is oxy or thio but an additional oxidation step can be included to convert a thio group to a sulfonyl group. The group Q is selected to be (a) a halo such as chloro, bromo, or iodo or (b) a group of formula —$OSO_2$—$R^4$ where $R^4$ is an alkyl, perfluoroalkyl, aryl, or aryl substituted with an alkyl, halo, or both. The group $R^2$ is a divalent group selected from an alkylene, heteroalkylene, arylene, or a combination thereof. The group $R^3$ is an alkyl and the group Rf is a perfluoroalkyl. Each $R^1$ group is typically an alkoxy or aryloxy in this reaction scheme. An alkoxy $R^1$ group can be unsubstituted or substituted with an aryl and an aryloxy $R^1$ group can be unsubstituted or substituted with a halo, alkyl, or both. The group Ar is an carbocyclic aromatic ring structure having at least 6 carbon atoms.

The aromatic bis(acyl) precursor of Formula (IV) has one -$L^1$H group. To prepare compounds of Formula (I) with n equal to in integer greater than one, a similar aromatic bis (acyl) precursor with more than one -$L^1$H group can be used.

Perfluoroalkylsulfonamido compounds of Formula (III) where Q is of formula —$OSO_2$—$R^4$ can be prepared by reaction of a fluorinated alcohol of Formula (V) with a sulfonyl halide of Formula (VI) as shown in Reaction Scheme B.

Reaction Scheme B

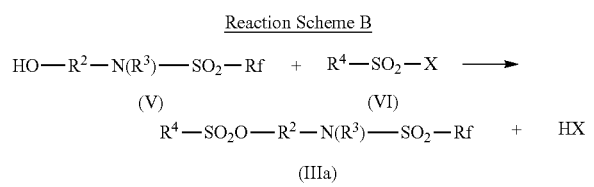

Many suitable fluorinated alcohols of Formula (V) are of formula $CF_3(CF_2)_3SO_2N(R^3)$—$R^2OH$ with $R^3$ selected from an alkyl having 1 to 4 carbon atom $R^2$ is an alkylene, heteroalkylene, or combination thereof. Exemplary fluorinated alcohols of Formula (V) include, but are not limited to, $CF_3(CF_2)_3SO_2N(CH_3)$—$CH_2CH_2OH$, $CF_3(CF_2)_3SO_2N(CH_3)$—$CH(CH_3)CH_2OH$, $CF_3(CF_2)_3SO_2N(CH_3)$—$CH_2CH(CH_3)OH$, $CF_3(CF_2)_3SO_2N(CH_3)$—$(CH_2)_4OH$, $CF_3(CF_2)_3SO_2N(C_2H_5)$—$CH_2CH_2OH$, $CF_3(CF_2)_3SO_2N(C_2H_5)$—$(CH_2)_6OH$, $CF_3(CF_2)_3SO_2N(C_3H_7)$—$CH_2OCH_2CH_2CH_2OH$, $CF_3(CF_2)_3SO_2N(C_3H_7)$—$CH_2CH_2OH$, $CF_3(CF_2)_3SO_2N(C_4H_9)$—$CH_2CH_2OH$, and $CF_3(CF_2)_3SO_2N(C_4H_9)$—$(CH_2)_4OH$. The preparation of suitable fluorinated alcohols of Formula (V) are described, for example, in U.S. Pat. No. 6,664,353 (Savu et al.), U.S. Pat. No. 6,852,781 (Savu et al.), and U.S. Pat. No. 7,361,782 (Klun et al.).

Exemplary sulfonyl halides of Formula (VI) include, but are not limited to, $CH_3SO_2Cl$, $CF_3SO_2F$, $C_4F_9SO_2F$, and $CH_3$—$C_6H_4$—$SO_2Cl$ (i.e., 4-toluenesulfonyl chloride).

Still other perfluoroalkylsulfonamido compounds of Formula (III) can be prepared as shown in Reaction Scheme C by reacting a perfluoroalkylsulfonamide of Formula (VIII) with a dihalide of Formula (VII). The group X in Formula (VII) is a halo such as chloro, bromo, or iodo. The groups Rf, $R^2$, and $R^3$ are the same as defined above. The perfluoroalkylsulfonamide of Formula (VIII) can be prepared by reacting a perfluoroalkylsulfonyl halide of Formula (IX) such as $C_4F_9SO_2F$ with a primary alkylamine (e.g., methylamine, ethylamine, and propylamine) as described in U.S. Pat. No. 6,852,781 (Savu et al.).

Reaction Scheme C

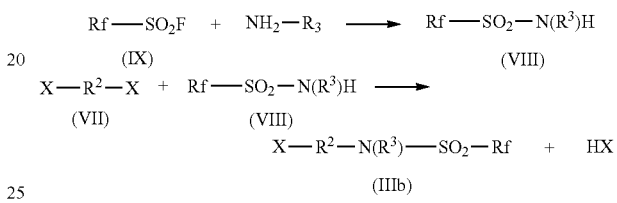

Exemplary dihalides of Formula (VII) include, but are not limited to, alkylene dihalides such as methylene dichloride, ethylene dichloride, ethylene dibromide, and propylene dichloride, $ClCH_2$—$C_6H_4$—$CH_2Cl$, and $ClCH_2$—$C_6H_4$—$C_6H_4$—$CH_2Cl$. Exemplary fluorinated sulfonamides of Formula (VIII) include, but are not limited to, $C_4F_9SO_2N(CH_3)H$ and $C_4F_9SO_2N(C_2H_5)H$.

As originally synthesized, the aromatic bis(acyl)-containing compound of Formula (I) often has $R^1$ groups that are alkoxy or aryloxy groups. This compound is a diester and can be hydrolyzed to prepare the aromatic bis(acyl)-containing compound where each $R^1$ group is hydroxyl. The resulting compound is a diacid and can be further reacted with $SO_2Cl$ to prepare the aromatic bis(acyl)-containing compound where each $R^1$ group is halo.

Some exemplary compounds of Formula (III), (IIIa), and (IIIb) include an $R^2$ group that is a combination of one or more arylene groups and one of more alkylene groups. More particularly, the compound of Formula (III) can be of Formula (II).

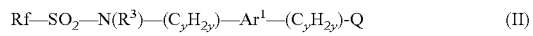

In Formula (II), $Ar^1$ is phenylene or diphenylene, Rf is a perfluoroalkyl, $R^3$ is an alkyl, and group Q is selected from a halo or group of formula —$OSO_2$—$R^4$ where $R^4$ is an alkyl, perfluoroalkyl, aryl, or aryl substituted with an alkyl. Some more specific compounds of both Formula (II) and Formula (III) are those of Formula (IIIc) and Formula (IIId).

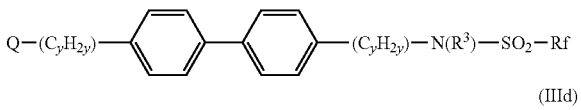

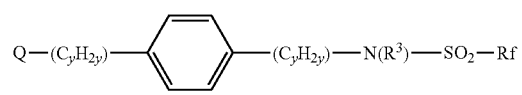

In these formulas, the groups Q, $R^3$, and Rf are the same as previously defined. The compounds of Formula (IIIc) and Formula (IIId) are of Formula (IIIa) where Q is of formula —O—$SO_2$—$R_4$ or of Formula (IIIb) where Q is halo. The variable y is an integer greater than or equal to 1 and is often an integer in the range of 1 to 10, in the range of 1 to 8, in the range of 1 to 4, in the range of 1 to 3, or in the range or 1 to 2. In some compounds of Formula (IIIc), $R^3$ is methyl, Rf is —$C_4F_9$, and y is an integer in the range of 1 to 4. Some exemplary compounds of Formulas (IIIc) and (IIId) are of Formulas (IIIe) and (IIIf) respectively.

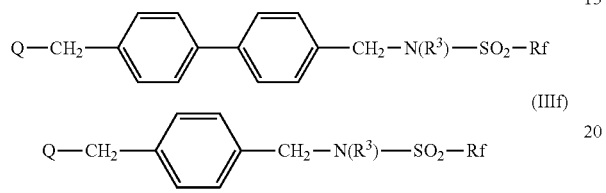

(IIIe)

(IIIf)

In some even more specific compounds, Rf in Formulas (IIIe) and (IIIf) are equal to —$C_4F_9$. Some more particular compounds of Formula (IIIe) and (IIIf) include, but are not limited to,

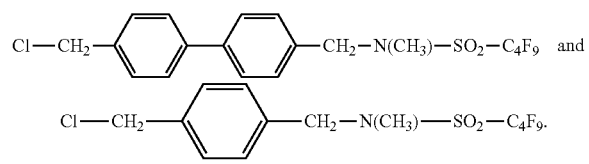

These compounds can be prepared with unusually high yields (e.g., greater than 70 percent) using Reaction Scheme C.

Aromatic bis(acyl)-containing compounds of Formula (Ib) (p and q are both equal to zero) can be prepared as shown in Reaction Scheme D by reacting an aromatic amine of Formula (X) with a perfluoroalkylsulfonyl fluoride of Formula (IX). The product of this reaction (i.e., Formula (XI) can be further reacted with $(CH_3)_2SO_4$ in the presence of sodium hydroxide to prepare the aromatic bis(acyl)-containing compound of Formula (Ib). As shown in Reaction Scheme D, the resulting compound has n equal to 1. To produce compounds of Formula (Ib) where n is greater than 1, an aromatic amine with more primary amino groups (—$NH_2$ groups) can be selected in place of the aromatic mono-amine of Formula (X).

Reaction Scheme D

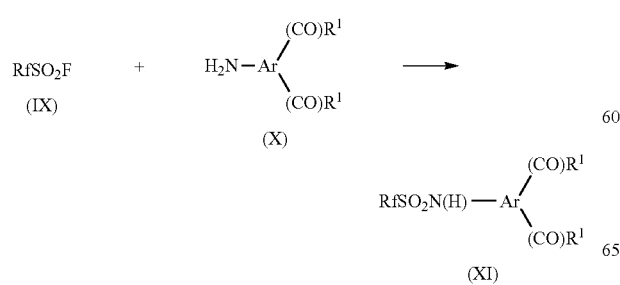

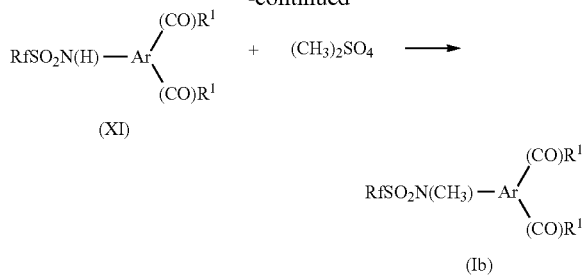

Exemplary compounds of Formula (X) include, but are not limited to, compounds of formula

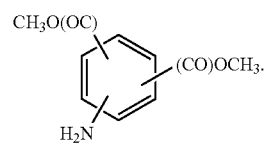

The groups —(CO)$OCH_3$ and —$NH_2$ can be bonded to any carbon of the benzene ring. Exemplary perfluoroalkylsulfonyl fluorides of Formula (IX) include, but are not limited to, $C_4F_9SO_2F$ or $C_6F_{13}SO_2F$.

Compounds of Formula (Ic) (p is equal to 1 and q is equal to zero in Formula (I)) can be prepared as shown in Reaction Scheme E.

Reaction Scheme E

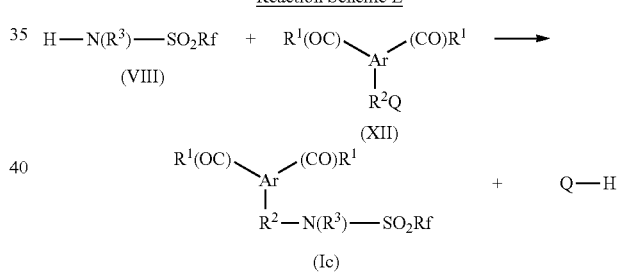

The groups $R^3$, Rf, $R^1$, Ar, $R^2$, and Q are the same as defined previously.

In another aspect, a fluorinated polyester is provided that is a condensation reaction product of a plurality of monomers that include (a) an aromatic bis(acyl)-containing compound of Formula (I) as described above and (b) a diol of Formula (XIII). The polymerization reaction is shown in Reaction Scheme F. The polymer is of Formula (XIV) where m is an integer greater than 1 and the asterisk indicates an attachment site to another group in the polymer such as another repeat unit or an end capping group.

Reaction Scheme F

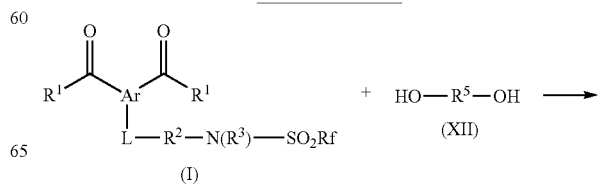

-continued

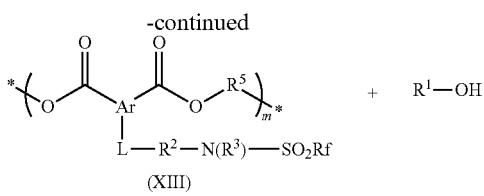
(XIII)

The groups Ar, $R^1$, $R^2$, $R^3$, Rf are the same as defined above. $R^5$ often includes an alkylene, heteroalkylene, arylene, or combination thereof and can optionally include perfluoroalkyl group, sulfonamido group, or both. Alkylene groups and heteroalkylene groups can be unsubstituted or substituted with an alkyl, halo, or aryl. Arylene groups can be unsubstituted or substituted with an alkyl, halo, or both. The variable m is an integer equal to at least 2. The variable m is usually equal to at least 5, at least 10, at least 20, at least 50, or at least 100.

Some suitable diols of Formula (XIII) are alkane diols such as, for example, 1,2-ethanediol, 1,2-propanediol, 3-chloro-1,2-propanediol, 1,3-propanediol, 1,3-butanediol, 1,4-butanediol, 2-methyl-1,3-propanediol, 2-methyl-1,2-propanediol, 2,2-dimethyl-1,3-propanediol, 2-ethyl-1,3-propanediol, 2,2-diethyl-1,3-propanediol, 1,5-pentanediol, 2-ethyl-1,3-pentanediol, 2,2,4-trimethyl-1,3-pentanediol, 3-methyl-1,5-pentanediol, 1,2-hexanediol, 1,5-hexanediol, 1,6-hexanediol, 2-ethyl-1,6-hexanediol, bis(hydroxymethyl)cyclohexane, 1,8-octanediol, bicyclo-octanediol, 1,10-decanediol, tricycle-decanediol, 1,12-dodecanediol, norbornanediol, and 1,18-octadecanediol.

Other suitable diols of Formula (XIII) are heteroalkylene diols with an oxygen heteroatom. Examples include but are not limited to, di(ethylene glycol), tri(ethylene glycol), tetra(ethylene glycol), di(propylene glycol), di(isopropylene glycol), tri(propylene glycol), poly(ethylene glycol)diol, poly(propylene glycols)diols, block copolymers of poly(ethylene glycol) and poly(propylene glycol), polycaprolactone diols.

Still other suitable diols of Formula (XIII) include an aromatic ring such as, for example, resorcinol, hydroquinone, 1,6-dihydroxynaphthalene, 2,5-dihydroxynaphthalene, 2,6-dihydroxynaphthalene, 2,7-dihydroxynaphthalene; 4,4'-biphenol, bisphenol A, 1,4-bis(hydroxymethyl)benzene, 4,4'-bis(hydroxymethyl)biphenyl, bis(4-hydroxy ethoxy phenyl) sulfone, bis(hydroxy ethyl ether) of bisphenol A, and bis(4-hydroxyphenyl)methane.

Yet other suitable diols of Formula (XIII) are fluoro-containing diols. Exemplary fluoro-containing diols include, but are not limited to, N,N-bis(2-hydroxyethyl)perfluorobutylsulfonamide, N-bis(hydroxybutyl)perfluorobutylsulfonamide, $C_4F_9SO_2N(C_3H_7)CH_2CH(OH)CH_2OH$; $C_4F_9CH_2(CO)N(CH_2CH_2OH)_2$ $C_4F_9OCH_2CH(OH)CH_2OH$, $C_4F_9CH_2CH_2CH_2OCH_2CH(OH)CH_2OH$, $(HOCH_2CF_2OC_2F_4O(CF_2)_4OC_2F_4OCF_2CH_2OH)$, and $(HOCH_2CF_2CF_2O(CF_2)_4OCF_2CF_2CH_2OH)$.

The polymerization reaction is often preceded by a transesterification reaction. During transesterification, the aromatic bis(acyl)-containing compound of Formula (I) and the diol of Formula (XIII) react to form a relatively low molecular weight prepolymer. The alcohol ($R^1OH$) by-product of the transesterification reaction is often removed. The transesterification reaction is typically performed at a temperature in the range of about 160° C. to about 260° C. at atmospheric pressure or greater. A catalyst such as tetra-n-butyl titanate (TBT) or the like can be added. The temperature is then held in the range of about 220° C. to 280° C. to complete the polymerization under reduced pressures such as less than 0.01 atmospheres, less than 0.005 atmospheres, or less than 0.001 atmospheres.

The ratio of the total number of equivalents of hydroxyl groups in the diol of Formula (XIII) to the total number of equivalents of groups of formula —$(CO)R^1$ in the aromatic bis(acyl)-containing compound of Formula (I) is typically 1:1 or 2:1. A slight excess of diol is often used to drive the reaction to completion, and the excess is removed after the completion of the polymerization reaction.

In another aspect, the fluorinated polyester of Formula (XIV) is an oligomeric material. As used herein, the terms "oligomer" or "oligomeric" refers to a polymeric material having no greater than 10 repeat units (i.e., the variable m in Formula (XIV) is no greater than 10). Often, the variable m is no greater than 8, no greater than 6, or no greater than 5. The oligomeric material can be prepared by adding a mono-functional end capping compound to terminate the polymerization reactions. Stated differently, a fluorinated polyester is provided that is a condensation reaction product of a plurality of monomers that include (a) an aromatic bis(acyl)-containing compound of Formula (I) as described above, (b) a diol, and (c) a mono-functional end capping compound that is reactive with the aromatic bis(acyl)-containing compound of Formula (I) or with the diol.

In this aspect, if the mono-functional end capping compound is capable of reacting with the compound of Formula (I), the reaction mixture used to form the fluorinated polyester contains a molar excess of the compound of Formula (I) relative to the diol. Enough of the mono-functional compound is added so that all of the —$(CO)R^1$ groups can react with either the diol or the mono-functional end capping compound. Conversely, if the mono-functional end capping compound is capable of reacting with the diol, the reaction mixture used to form the fluorinated polyester contains a molar excess of the diol relative to the compound of Formula (I). Enough of the mono-functional compound is added so that all of the diol is reacted with either the compound of Formula (I) or the mono-functional end capping compound.

The mono-functional end capping compound is often a mono-functional alcohol that can react with one of the —$(CO)R^1$ groups of the compound of Formula (I). Any suitable fluorinated or non-fluorinated mono-functional alcohol can be used. In some embodiments, the mono-functional alcohol is an alkanol having 1 to 22 carbon atoms. In other embodiments, the mono-functional alcohol is a fluoro-containing alcohol. For example, the fluoro-containing alcohol can have a perfluoroalkyl group. More perfluoroalkyl groups introduced into the polyester can often further enhance the oil and water repellency of the resulting polymeric materials. Examples of fluoro-containing mono-functional end capping compounds include, for example, $C_4F_9SO_2N(CH_3)$—$CH_2CH_2OH$, $C_4F_9SO_2N(H)$—$CH_2CH_2OH$, $C_4F_9SO_2N(CH_3)(CH_2)_4OH$, $C_4F_9SO_2N(C_2H_5)CH_2CH_2OH$, $CF_3(CF_2)_3$ $SO_2N(CH_3)CH_2CH(CH_3)OH$, $CF_3(CF_2)_3SO_2N(CH_3)CH(CH_3)CH_2OH$, $CF_3(CF_2)_3SO_2N(C_2H_5)CH_2CH_2OH$, $C_2F_5O(C_2F_4O)_3CF_2(CO)NHC_2H_4OH$, $C_4F_9CH_2CH_2OH$, N-methyl-N-(4-hydroxybutyl)perfluorohexanesulfonamide, 1,1,2,2-tetrahydroperfluorooctanol, 1,1-dihydroperfluorooctanol, c-$C_6F_{11}CH_2OH$, $C_4F_9OC_2F_4OCF_2CH_2OCH_2CH_2OH$, $C_3F_7CON(H)CH_2CH_2OH$, 1,1,2,2,3,3-hexahydroperfluorodecanol, $CF_3O(CF_2CF_2O)_{1-36}CF_2CH_2OH$, and $C_3F_7O(CF(CF_3)CF_2O)_{1-36}CF(CF_3)CH_2OH$.

Alternatively, the mono-functional end capping compound is often a mono-functional ester, mono-functional carboxylic acid, or mono-functional acyl halide that can react with one of the hydroxyl groups of the diol. Any of these mono-functional end capping compounds can be fluorinated or non-fluorinated. Suitable non-fluorinated, mono-functional carboxylic acids include, but are not limited to, butanoic acid, pentanoic acid, hexanoic acid, benzoic acid, and phenylacetic acid. Suitable fluorinated mono-functional carboxylic acids include, but are not limited to, perfluorobutanoic acid ($C_3F_7(CO)OH$), 12-(2-perfluoroisopropoxyperfluoroethyl)dodecanoic acid, 6-(2-perfluorocyclobutoxyperfluoroethyl)hexanoic acid, 4-(2-bis(perfluoroisopropyl)fluoromethoxyperfluoroethyl) butanoic acid, 2-(N-(ethyl)perfluorobutanesulfonamido)acetic acid, N-methyl-perfluorobutanesulfonamidobutyric acid, and 2-(N-(methyl)perfluorobutanesulfonamido)acetic acid.

The fluorinated polyesters can be dissolved in a suitable solvent to prepare a coating composition that can be applied to a surface of a substrate. The solvent can be removed after application of the coating to the substrate. Suitable solvents include, but are not limited to, alcohols, esters, ethers, glycol ethers, amides, ketone, hydrocarbons, chlorohydrocarbons, hydrofluoroethers, chlorocarbons, and mixtures thereof. The coating compositions often contain 0.1 to 10 weight percent, 0.1 to 5 weight percent, or 0.5 to 5 weight percent fluorinated polyester.

The coating composition can be applied to any suitable substrate. In some embodiments, the coating composition is applied to fibers such as woven fabrics, knit fabrics, nonwoven fabrics, textiles, carpets, leather, or paper. Other substrates include, but are not limited to, glass, ceramic, masonry, concrete, natural stone, metals, wood, plastic, and painted surfaces. The substrates can have flat or curved surfaces and can be particles or granules.

The coating compositions can be applied to the substrate using any suitable application method such as, for example, spraying, padding, dipping, roll coating, or brushing. When coating flat substrates of appropriate size, knife-coating or bar-coating methods can be used to ensure uniform coatings of the substrate. The thickness of the coating can be any suitable thickness needed to achieve the desired properties such as the desired repellency. This thickness of the coating can often be adjusted without compromising the desirable characteristics of the substrate. For example, the coatings can be in the range of a few microns (e.g., 1 to 5 microns) up to about 50 microns or even greater, up to about 30 microns, up to about 20 microns, or up to about 10 microns.

The polyester can also be heated and then extruded or molded. Any methods know in the art can be used. In some embodiments, the fluorinated polyesters are extruded to form a clear film that is suitable for use in optical applications. The polyesters are often extruded at temperatures in the range of about 150° C. to about 300° C. or in the range of about 150° C. to about 250° C.

The fluorinated polyesters can have low surface energy as indicated by its water and oil repellency. Compared to many non-fluorinated polyesters, the contact angle with both water and hexadecane tends to be greater. That is, these polyesters can be used to provide a surface that is water and oil repellant. Such surfaces tend to remain cleaner and are more easily cleaned than many non-fluorinated surfaces.

The refractive index of the fluorinated polyesters is often lower than non-fluorinated polyesters. The polyesters tend to have good clarity and can be used in optical applications. The polyesters can be used, for example, in optical films where the combination of low refractive index, optical clarity, and easy clean characteristics are desirable.

In another aspect of the invention, there is provided a method of making certain compounds (referred to herein as monosubstituted-arylene compounds) of Formula (XV):

$$Rf^1\text{-}L^2\text{-}CH_2\text{---}Ar^2\text{---}CH_2\text{---}W \qquad (XV)$$

wherein: $Ar^2$ is a phenylene (—$C_6H_4$—) or diphenylene (—$C_6H_4$—$C_6H_4$—) (in certain embodiments, $Ar^2$ is diphenylene); $Rf^1$ is a perfluoroalkyl with optional O or N within the chain; $L^2$ is selected from —O—, —$SO_2$—, —$CH_2$—O—, —$C_2H_4$—O—, —$C_2H_4$—S—, and —$SO_2$—N($R^6$)—; $R^6$ is a C1-C4 alkyl; and W is a leaving group.

In this context, the term "leaving group" refers to an atom or group of atoms that departs with a pair of electrons in heterolytic bond cleavage. Typically, this is a stable anion of a strong acid, such as, for example, halides (fluoride, chloride, bromide, or iodide) and sulfonate esters (e.g., methanesulfonate). The term "monosubstituted-arylene compound" refers to a compound in which one of the two leaving groups of an arylene-containing precursor has been replaced by one fluorochemical group.

In certain embodiments of Formula (XV), the group W is preferably selected from halide and pseudohalide groups. More preferably, the group W is selected from Cl, Br, or —$OSO_2R^7$, wherein $R^7$ is an alkyl, aryl, fluorinated alkyl, or combination thereof (e.g., methyl, tolyl, and benzyl).

In compounds of Formula (XV), the group $Rf^1$ is a perfluoroalkyl with optional O or N within the chain. Suitable perfluoroalkyl groups often have 1 to 60 carbon atoms, 1 to 30 carbon atoms, 1 to 20 carbon atoms, 1 to 10 carbon atoms, 1 to 8 carbon atoms, 1 to 6 carbon atoms (for certain embodiments 3 to 6 carbon atoms), or 1 to 4 carbon atoms. In certain embodiments, the $Rf^1$ group is of the formula $C_{xx}F_{2xx+1}(OC_{yy}F_{2yy})_{aa}OC_{pp}F_{2pp}$—, wherein xx is 1 to 4, yy is 1 to 4, pp is 1 to 4, and aa is 0 to 20 (for certain embodiments, 4 to 20), wherein in any one molecule each variable is independently selected. In certain embodiments, the $Rf^1$ group is of the formula $C_3F_7(OCF_2CF(CF_3))_{aa}OCF(CF_3)$—, wherein aa is 4 to 20. In many embodiments, the group $Rf^1$ is —$C_3F_7$, —$C_4F_9$, —$C_6F_{13}$, or —$C_8F_{17}$. More particularly, the $Rf^1$ is —$C_3F_7$, —$C_4F_9$, or —$C_6F_{13}$. Even more particularly, the $Rf^1$ group is —$C_4F_9$ or —$C_6F_{13}$.

In compounds of Formula (XV), the group $L^2$ is selected from —O— (an oxy group), —$SO_2$— (a sulfonyl group), —$CH_2$—O—, —$C_2H_4$—O—, —$C_2H_4$—S—, and —$SO_2$—N($R^6$)—. In certain embodiments, the group $L^2$ is selected from —$CH_2$—O—, —$C_2H_4$—O—, and —$SO_2$—N($R^6$)—. In certain embodiments, $L^2$ is —$SO_2$—N($R^6$)— or —$C_2H_4$—O—.

In compounds of Formula (XV), the group $R^6$ is a C1-C4 alkyl. In certain embodiments, $R^6$ is —$CH_3$.

Such compounds can be prepared using a method that involves combining a base with a compound of Formula (XVI) $Rf^1$-$L^2$-H, a compound of Formula (XVII) W—$CH_2$—$Ar^2$—$CH_2$—W, and an organic solvent, as exemplified by Examples 2, 11, and 12. Preferably, the compounds of Formulas (XVI) and (XVII) are in a solution with the organic solvent and the base is added to the solution. The reaction (e.g., addition of base to solution of compounds of Formulas (XVI) and (XVII)) is carried out over a period of time effective to form the monosubstituted-arylene compound of Formula (XV).

In compounds of starting material Formula (XVI): $Rf^1$ is a perfluoroalkyl with optional O or N within the chain (with exemplary and preferred $Rf^1$ groups as discussed herein for compounds of Formula (XV)); and $L^2$ is selected from —O—, —$SO_2$—, —$CH_2$—O—, —$C_2H_4$—O—, —$C_2H_4$—S—, and —$SO_2$—N($R^6$)— wherein $R^6$ is a C1-C4 alkyl (preferably, $R^6$ is —$CH_3$). In certain embodiments, the group $L^2$ is selected from —$CH_2$—O—, —$C_2H_4$—O—, and —$SO_2$—N($R^6$)—. In certain embodiments, $L^2$ is —$SO_2$—N($R^6$)— or —$C_2H_4$—O—.

In compounds of starting material Formula (XVII): $Ar^2$ is a phenylene or diphenylene (preferably, a diphenylene); and W is a leaving group (with exemplary and preferred W groups as discussed herein for compounds of Formula (XV)). In compounds of Formula (XVII), the W groups can be independently selected.

In certain embodiments of the method of making a mono-substituted-arylene compound of Formula (XV) (e.g., for sulfonamide compounds), the base is more basic than sodium carbonate. In certain embodiments of this method, the base is an organic base. In certain embodiments of this method, the organic base is selected from 1,8-diazabicyclo[5.4.0]undec-7-ene, 1,5-diazabicyclo[4.3.0]non-5-ene, and $(R^8)_4NOH$ wherein $R^8$ is C1-C4 alkyl. In certain methods, the base is an inorganic base, such as NaOH or NaH.

In certain embodiments of the method of making a mono-substituted-arylene compound of Formula (XV), the organic solvent is selected from acetone, THF, DMF, toluene, or mixtures thereof. Exemplary organic solvents are ones that will dissolve the monosubstituted-arylene compound of Formula (XV) at a temperature of, e.g., 25° C. to 50° C. The temperature of the reaction between starting materials of Formulas (XVI) and (XVII) is not particularly critical. That is, a range of temperatures can be used as can be determined by one of skill in the art that would be practical, effective, and efficient. For example, temperatures down to 0° C. can be used, as well as refluxing temperatures of the solvent(s). Typically, a temperature of 25° C. to 50° C. is used.

In certain embodiments of the method of making a mono-substituted-arylene compound of Formula (XV), the base is added to a solution of the starting materials of Formulas (XVI) and (XVII). Alternatively, however, the base can be added to one of the reactants, typically the starting material of Formula (XVI), and then the mixture can be added to starting material of Formula (XVII) W—$CH_2$—$Ar^2$—$CH_2$—W. Typically, the base (whether added to a solution of both starting materials or added in combination with the starting material of Formula (XVI)) is added relatively slowly such that the compound of Formula (XVII) W—$CH_2$—$Ar^2$—$CH_2$—W is in excess relative to the reactive nucleophile. Typically, the base is added over a period of at least 1 hour, and often at least 2 hours, although shorter periods of time can be used.

In certain embodiments of the method of making a mono-substituted-arylene compound of Formula (XV), such compound is formed in a yield of at least 70 mole-%.

In certain embodiments of the method of making a mono-substituted-arylene compound of Formula (XV), such compound is formed at a purity level of at least 70 wt-%, based on the total weight of solids.

In certain embodiments of the method of making a mono-substituted-arylene compound of Formula (XV), such compound is isolated from the reaction mixture prior to further use.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Solvents and other reagents used were obtained from Aldrich Chemical Company, Milwaukee, Wis. unless otherwise noted.

Test Methods

Measuring Contact Angles

Measurements were made using as-received reagent-grade hexadecane and deionized water filtered through a filtration system (obtained from Millipore Corporation, Billerica, Mass.), on a video contact angle analyzer (available as product number VCA-2500XE from AST Products, Billerica, Mass.). Reported values are each the average result obtained from the measurement of at least three drops that were measured on the right and the left sides. Drop volumes were 5 µL (microliters) for static contact angle measurements and 1 to 3 µL for advancing and receding contact angle measurements. For hexadecane, only advancing and receding contact angles are reported because static and advancing values were found to be nearly equal.

Differential Scanning Calorimeter (DSC) Analysis

A sample (7 to 10 milligrams) of the fluorinated polyester was placed in a TZERO aluminum pan and lid (obtained from TA Instruments, New Castle, Del.) and was run in a TA Q2000 DSC (TA Instruments, New Castle, Del.) under a nitrogen flow of 50 mL per minute. The sample was equilibrated at 30° C., heated at 20° C. per minute to 290° C., held at 290° C. for 3 minutes, cooled at 20° C. per minute to 30° C., heated at 20° C. per minute to 290° C.

Measuring Refractive Index

The refractive index was measured using a Metricon Prism coupler (Metricon Corporation, Pennington, N.J.) in the MD (stretch direction, i.e., x-direction), TD (perpendicular to but in the same plane as the stretch direction, i.e., y-direction), and TM (perpendicular to the x-y plane, i.e., z-direction) directions. MD and TD are in-plane directions and TM is normal to the film surface if the sample was prepared as a film. The refractive indices of MD, TD and TM were averaged to give a bulk refractive index.

Example 1

The fluorinated diester Compound C was prepared according to the following general reaction scheme:

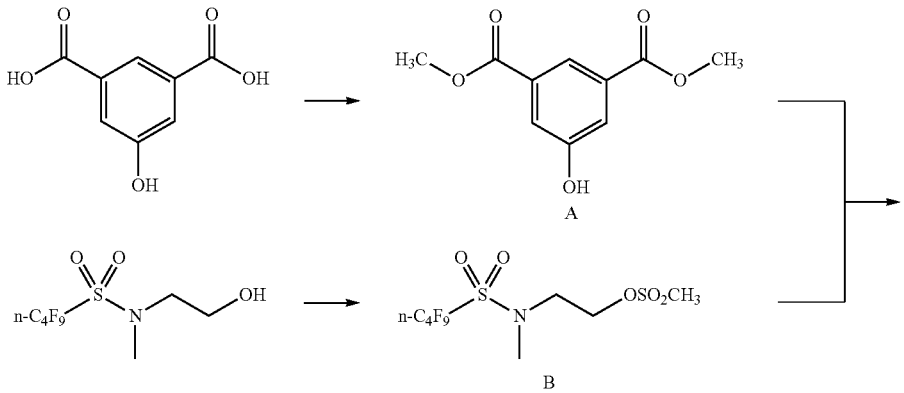

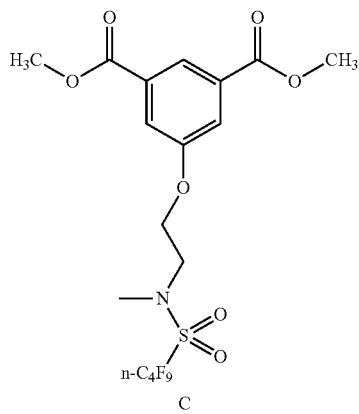

C

Synthesis of Compound A

Concentrated sulfuric acid (50 mL) was added to a solution of 5-hydroxyisophthalic acid (250 grams, 1.54 moles) in methanol (750 mL). The resulting solution was heated at reflux for 6 hours and then concentrated under reduced pressure of about 0.013-0.052 atmospheres. The resulting oily white solid was dissolved in ethyl acetate (500 mL) and washed consecutively with a saturated aqueous sodium bicarbonate solution, water, and then with a saturated sodium chloride solution. The resulting organic layer was dried over magnesium sulfate, filtered, and concentrated under reduced pressure of about 0.013-0.052 atmospheres. The residue was the desired diester Compound A (56 grams, 78 percent yield) with a melting point of 165-166° C.

Synthesis of Compound B

The fluorinated alcohol $C_4F_9SO_2N(Me)CH_2CH_2OH$ was prepared as described in U.S. Pat. No. 6,664,354 B2 Example 2 (part A). $C_4F_9SO_2N(Me)CH_2CH_2OH$ (535.5 grams, 1.5 mole), $CH_3SO_2Cl$ (182.3 grams, 1.56 mole, obtained from GSF Chemicals, Powell, Ohio), and 2000 mL of ethyl acetate (obtained from J T Baker, Phillipsburg, N.J.) were charged into a three-necked flask with mechanical stirring. After the reactant solution was cooled to 0° C. in a water-ice bath, $Et_3N$ (1.56 mole, 157.6 grams) was added dropwise. The mixture was allowed to react overnight. The reaction product solution was washed consecutively with saturated aqueous sodium bicarbonate solution, water, and then a saturated sodium chloride solution. The organic layer was dried over anhydrous magnesium sulfate, filtered, and concentrated under reduced pressure of about 0.013-0.052 atmospheres. The residue was the desired Compound B (762 grams, 95 percent yield).

Synthesis of Compound C

Compound A (0.3 mole, 63 grams), compound B (0.3 mole, 130.5 grams), potassium carbonate (0.3 mole, 41.4 grams), 18-crown-6 (0.03 grams) (Aldrich, Milwaukee, Wis.), butanone 700 mL, and N,N'-dimethyl formamide (700 mL, obtained from EMD Chemical Inc. Darmstadt, Germany) were loaded into a three-necked flask equipped with mechanical stirring. The mixture was refluxed for 5 hours and then was poured into water. Ethyl acetate (100 mL) was added to extract the product. The organic layer was washed consecutively with aqueous sodium hydroxide solution, water and saturated sodium chloride solution. The organic layer was dried using magnesium sulfate, filtered and concentrated under reduced pressure of about 0.013-0.052 atm. The residue was recrystallized from ethanol and the desired compound C (102 g, 63% yield) was prepared.

Example 2

The fluorinated diester Compound H was prepared according to the following general reaction scheme:

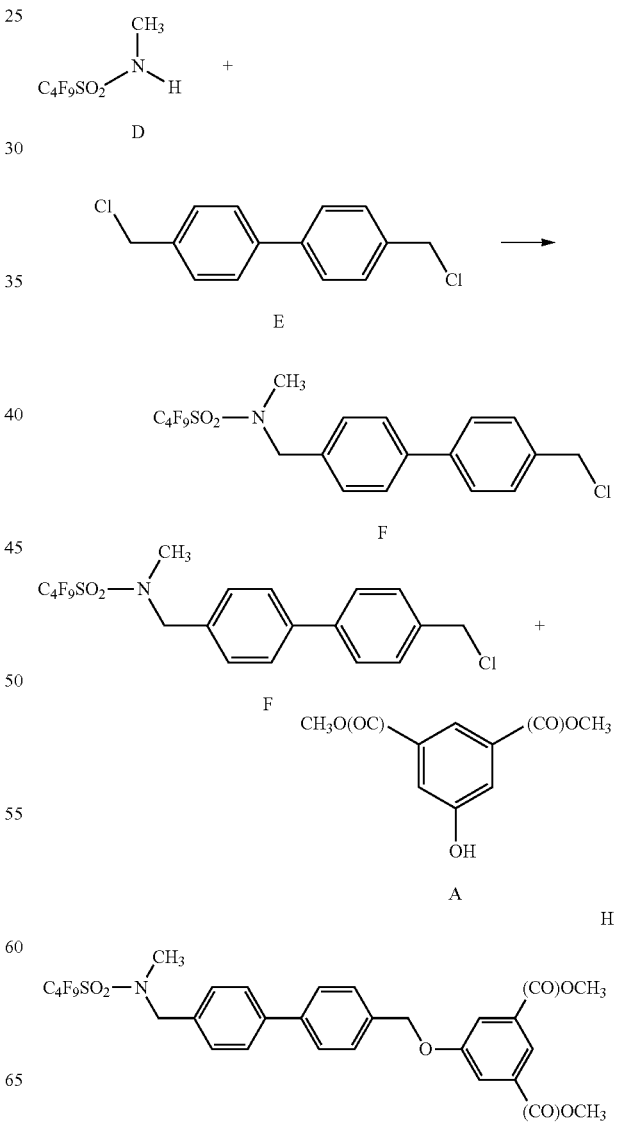

Compound D was prepared as described in Example 1 of U.S. Patent Application Publication 2003/0139549 A1 (Savu et al.). Compound D (0.15 moles, 47 grams) and compound E (0.15 moles, 37.7 grams) (Aldrich, Milwaukee, Wis.) were dissolved in 250 mL acetone. The solution was heated to 50° C. A solution of $(C_4H_9)_4NOH$ (55 weight percent in water, 0.15 mole, 70.8 grams) was added slowly during 3 hours while the solution temperature was kept at 50° C. After the addition was finished, the reaction mixture was kept for another 1 hour at 50° C. The solid was filtered off and washed with 100 mL of acetone. The acetone was removed using a rotary evaporator. The solid was re-dissolved into ethyl acetate, washed with water, and dried over anhydrous magnesium sulfate. Removal of solvent using a rotary evaporator gave 60 grams of Compound F (76 percent yield and 94 weight percent purity).

Compound F (0.04 moles, 21 grams) prepared as described above, Compound A (0.04 mole, 8.4 grams), potassium carbonate (0.06 moles, 8.4 grams) and dimethyl sulfoxide, DMSO (40 mL) were charged into a flask. The solution was heated at 40° C. for 6 hours. The solution was diluted by ethyl acetate, washed with water, and dried over anhydrous magnesium sulfate. Evaporation of solvent with a rotary evaporator yielded a solid crude product. The crude product was recrystallized from a mixture of methanol (50 mL) and ethyl acetate (20 mL). Approximately 18 grams of pure Compound H was produced.

Example 3

The fluorinated diester Compound K was prepared according to the following general reaction scheme:

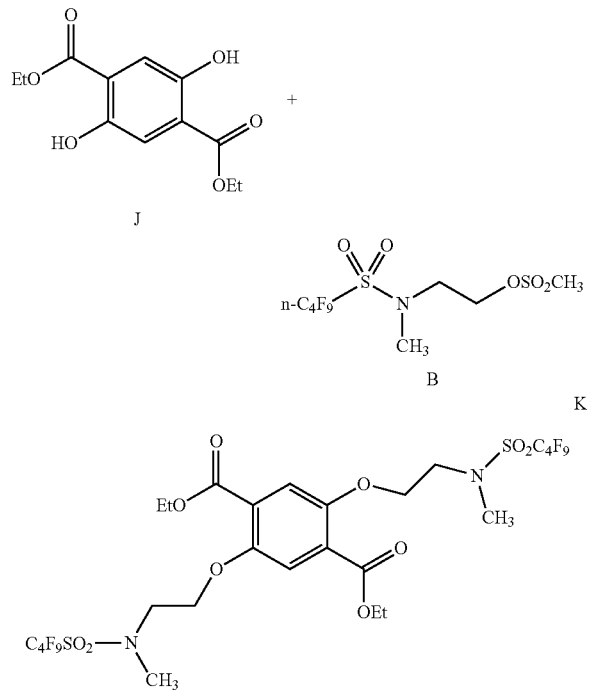

Compound J (0.1 mole, 25.4 grams), Compound B (0.2 mol, 87 g) prepared as described in Example 1, potassium carbonate (0.3 mole, 41.4 grams), N,N'-dimethylformamide (300 mL, obtained from EMD Chemical Inc. Darmstadt, Germany) were placed in a three-necked flask equipped with mechanical stirring. The mixture was heated to 120° C. for 10 hours and then was poured into water. Ethyl acetate (100 mL) was added to extract the product. The organic layer was washed consecutively with aqueous sodium hydroxide solution, water, and a saturated sodium chloride solution. The organic layer was dried over magnesium sulfate, filtered, and concentrated under reduced pressure of about 0.013-0.052 atmospheres. The residue was recrystallized from methanol twice and the desired Compound K (51.6 grams, 55 percent yield) was prepared.

Examples 4-8

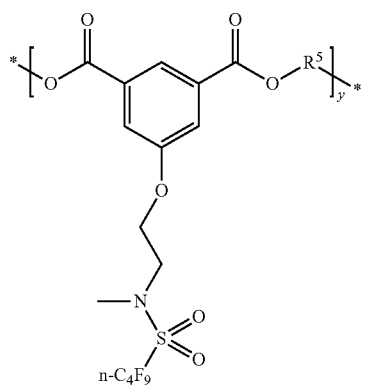

For Examples 4 to 8, the fluorinated diester Compound C (0.03 mmoles) prepared in Example 1, a diol (0.066 mmoles), and 500 ppm tetra-n-butyl titanate (TBT) were added to a three neck flask equipped with $N_2$ inlet, mechanical stirrer and a condenser. The diol was $HO—CH_2CH_2—OH$ for Example 4, $HO—CH_2CH_2CH_2CH_2—OH$ for Example 5, $HO—(CH_2)_{12}—OH$ for Example 6, $(HO—CH2CH_2)_2NSO_2C_4F_9$ for Example 7, and $HO—CH_2C(CH_3)_2CH_2—OH$ for Example 8. $R^5$ in the above formula is equal to the divalent group $—CH_2CH_2—$ for Example 4, the divalent group $—CH_2CH_2CH_2CH_2—$ for Example 5, the divalent group $—(CH_2)_{12}—$ for Example 6, the divalent group $n-C_4F_9SO_2N(CH_2—)_2$ for Example 7, and the divalent group $—CH_3C(CH_3)_2CH_2—$ for Example 8. The diol used in Example 7 can be prepared as described in Example 8 of U.S. Pat. No. 3,787,351 (Olson) except that an equimolar amount of $C_4F_9SO_2NH_2$ is substituted for $C_8F_{17}SO_2NH_2$. The compound $C_4F_9SO_2NH_2$ can be prepared by reacting $C_4F_9SO_2F$ with an equimolar amount of $NH_3$.

The mixtures were heated to 220° C. gradually (over about 40 minutes). The methanol started to distill when the temperature was about 180 to 210° C. The reaction was kept at 220 to 230° C. for 2 hours to complete the transesterification reaction. Vacuum was applied and gradually increased over about 30 minutes to about 0.0003 atmospheres. The temperature was raised to 230 to 260° C. and held for 3 hours. The melt viscosity increased during the polymerization. The reaction was stopped and polymer was isolated.

The resulting polyesters were then characterized by measuring the melting point ($T_m$) and glass transition temperature ($T_g$) using the above described DSC analysis method described above. The polyesters were also characterized by measuring the refractive indexes using the process for determining the refractive index described above. Table 1 summarizes the $T_m$, $T_g$ and refractive indexes of Example 4 to 8 as well as a commercially available PET (PET-9921 obtained from Eastman Chemical, Kingsport, Tenn.).

TABLE 1

| Example No. | $T_g$ (° C.) | $T_m$ (° C.) | Refractive Index |
|---|---|---|---|
| Example 4 | 73.3 | 191.6 | 1.473 |
| Example 5 | 50.9 | | 1.470 |
| Example 6 | 17.6 | | 1.473 |
| Example 7 | 120.2 | 151.5 | 1.443 |
| Example 8 | 62.9 | | 1.469 |
| PET-9921 | 78.8 | 241.6 | 1.572 |

The fluorinated polyester of Example 6 was dissolved in methylene chloride. The fluorinated polyesters of Examples 4, 5, 7, and 8 were dissolved in cyclopentanone. The percent solids of these solutions were about 5 weight percent. These five solutions were cast into films having a thickness of about 0.1 to 0.3 millimeters. The films were prepared by spreading the solutions on a glass plate and drying in air for 24 hours. The dried samples were further dried in vacuum box for 24 hours at room temperature and then at 60° C. for another 48 hours. After drying, the samples were rinsed for 1 minute by hand agitation in isopropyl alcohol (IPA), which was allowed to evaporate before measuring the water and hexadecane contact angles.

The water ($H_2O$) and hexadecane (HD) contact angles were measured using the method described above. Table 2 and 3 summarize the water and hexadecane contact angles of Example 4- to 8 polyesters as well as two commercially available polyesters PET (PET-9921 obtained from Eastman Chemical, Kingsport, Tenn.) and polymeric material formed from MeFBSEA, which is referred to as poly-MeFBSEA.

MeFBSEA refers to N-methyl-perfluorbutanesulfonylethyl acrylate ($C_4F_9SO_2N(CH_3)CH_2CH_2O(CO)CH=CH_2$) and was prepared as described in Example 2 of U.S. Pat. No. 6,852,781 (Savu et al.). Poly-MeFBSEA was prepared by placing 10.0 grams MeFBSEA, 100 milligrams 2,2'-azobis (2-methylbutyronitrile (commercially available from DuPont, Wilmington, Del. under the trade designation VAZO 67), and 30 grams ethyl acetate in a 125 mL polymerization bottle. The mixture was purges with 1 liter per minute nitrogen for 1 minute and then sealed. The bottle was rotated in a water bath at 60° C. for 24 hours. The resulting polymeric material was a viscous solution.

The contact angles obtained for the five prepared films were compared to the contact angles for a commercially available polyethylene terephthalate film (PET-9921 from Eastman, Kingsport, Tenn.) and for the fluorinated polymer (poly-MeFBSEA)

TABLE 2

| Example No. | $H_2O$ Contact Angle (Static) | $H_2O$ Contact Angle (Advance) | $H_2O$ Contact Angle (Receding) |
|---|---|---|---|
| Example 4 | 110.2 | 115.6 | 104 |
| Example 5 | 112.5 | 125.4 | 95.2 |
| Example 6 | 110 | 119.5 | 64 |
| Example 7 | 112 | 113.5 | 101.4 |
| Example 8 | 104 | 102 | 84 |
| PET-9921 | 75 | 79 | 44 |
| PMeFBSEA | | 116 | 66 |

TABLE 3

| Example No. | HD Contact Angle (Advance) | HD Contact Angle (Receding) |
|---|---|---|
| Example 4 | 68.6 | 65.2 |
| Example 5 | 73.2 | 56.2 |
| Example 6 | 72.7 | 56.4 |
| Example 7 | 75 | 70 |
| Example 8 | 62.3 | 54 |
| PET-9921 | <20 | <20 |
| PMeFBSEA | 74 | 59 |

Example 9

A film of fluorinated polyester of Example 4 was prepared in a 0.75 inch (1.91 cm) Brabender laboratory extruder with a non-mixing extrusion screw (obtained from Brabender Instruments Inc., New Jersey). The screw speed was 100 revolutions per minute with a torque of 0.75 N-m. After melting and being transported through the extruder through three zones of the extrusion barrel (zones 1, 2, and 3), the extrudate was forced through a 6 inch (15.24 cm) flat cast extrusion die to form a molten film at the desired settings. The temperatures of zones 1, 2, 3, the adapter, and die within the extruder were all set at 400° C. (205° C.). The resulting molten extrudate was passed through a chilled roll stack to cool the extrudate into a solidified film. The line speed was adjusted to produce a solidified film with a caliper of approximately 4 mils (100 microns).

The resulting extruded films were tested for their water and hexadecane contact angles using the method described above. The static contact angle for water was 104. The advancing contact angle was 115.6 for water and 68.6 for HD. The receding contact angle was 110.2 for water and 65.2 for HD.

Example 10

5.8847 grams of the fluorinated diester Compound K (0.006310 mmoles) prepared in Example 3, 0.7833 grams of ethylene glycol (Aldrich, 0.01262 mmoles), 0.9015 g of $CF_3(CF_2)_3SO_2N(CH_3)$—$CH_2CH_2OH$ (0.002524 mmoles), and 29 milligrams of tetra-n-butyl titanate (TBT, about 500 ppm, Aldrich) were added to a three neck flask equipped with $N_2$ inlet, mechanical stirrer and a condenser.

The mixtures were heated to 235° C. gradually over about 150 minutes. The ethanol started to distill out when the temperature was about 235° C. The reaction was kept at 235 to 250° C. for 1.5 hours to complete the transesterification reaction. Vacuum was applied and gradually increased over about 30 minutes to about 0.00066 atmospheres. The temperature was held at 250° C. for two hours. The melt viscosity slightly increased during the polymerization. The reaction was stopped and polymeric material was drained.

The polymeric material was characterized using DSC. The glass transition temperature was 76° C. and melting temperature was 177° C.

Example 11

Preparation of 4-(heptafluorobutoxymethyl)-4'-chloromethylbiphenyl

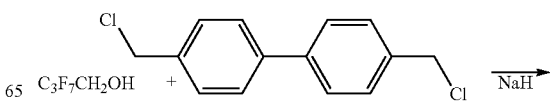

$C_3F_7CH_2$—O—[biphenyl]—$CH_2Cl$

A mixture of 20.0 g (0.1 mol) $C_3F_7CH_2OH$ and 60 mL DMF was treated with 4.0 g of 60% NaH/mineral oil in small portions at <10° C. The resulting solution was added dropwise over 1 hr to a solution of 25.1 g (0.1 mol) 4,4'-bis (chloromethyl)biphenyl in 110 mL DMF at 50° C. After 5 hr, the mixture was poured into 1 liter (L) water and the resulting white solid collected by filtration. GLC (thermal conductivity detector) showed two new materials (5% and 39%) and 50% unreacted starting dichloride. GC/MS confirmed these as 4,4'-bis(heptafluorobutoxymethyl)biphenyl and 4-(heptafluorobutoxymethyl)-4'-chloromethylbiphenyl, respectively. The solid (35.4 g) was dissolved in 600 mL boiling hexane. A granular precipitate (5.8 g) formed on cooling to 23° C. The supernatant liquid was evaporated to yield 17.5 g, 10% diether, 60% monoether and 30% dichloride.

Example 12

Preparation of 4-((1H,1H,2H,2H-perfluoro-1-octyl) oxymethyl)-4'-chloromethylbiphenyl $C_6F_{13}CH_2CH_2OH$ + Cl—$CH_2$—[biphenyl]—$CH_2$—Cl $\xrightarrow{NaH}$ $C_6F_{13}CH_2CH_2$—O—[biphenyl]—$CH_2Cl$ A boiling solution of 40.0 g (0.1 mol) 1H,1H,2H,2H-perfluoro-1-octanol and 25.1 g (0.1 mol) 4,4'-bis(chloromethyl) biphenyl in 150 mL THF was treated dropwise over 1 hr with 8.0 g 50% NaOH/water. The reaction was stopped at 2.5 hr and quenched in water and extracted with methylene chloride. This material (61.5 g) was a pale yellow solid with some liquid, $C_6F_{13}C_2H_4OH$ by GLC. Trituration with hexane left 19.3 g solid, shown by GLC to be 55% dichloride plus two new products. The hexane was evaporated to 36.4 g. Trituration with perfluoromethylmorpholine left 26.4 g solid. GC/MS showed the major component (74%) to be the desired 4-((1H,1H,2H,2H-perfluoro-1-octyl)oxymethyl)-4'-chloromethylbiphenyl with the diether (4,4'-bis((1H, 1H,2H,2H-perfluoro-1-octyl)oxymethyl)biphenyl as minor component.

We claim:
1. A compound of Formula (I)

$$(Rf—SO_2—N(R^3)—(R^2)_p—(L)_q)_n—Ar\begin{matrix}(CO)R^1\\(CO)R^1\end{matrix} \quad (I)$$

wherein
each $R^1$ is independently a halo, hydroxyl, alkoxy, or aryloxy, wherein the alkoxy is unsubstituted or substituted with an aryl and the aryloxy is unsubstituted or substituted with a halo, alkyl, or combination thereof;

Ar is an aromatic ring structure having at least 6 carbon atoms;
L is a single bond, oxy, thio, sulfonyl;
$R^2$ is a divalent group selected from an alkylene, heteroalkylene, arylene, or combination thereof;
$R^3$ is an alkyl;
Rf is a perfluoroalkyl,
n is an integer in a range of 1 to 4;
p is an integer equal to 1;
q is an integer equal to 1.

2. The compound of claim 1, wherein the compound of Formula (I) is a compound of Formula (Id) or (Ie)

$$\text{(Id)}\quad\text{aromatic ring with } LR^2N(R^3)SO_2Rf,\ (CO)R^1,\ R^1(OC)$$

$$\text{(Ie)}\quad\text{aromatic ring with } LR^2N(R^3)SO_2Rf,\ (CO)R^1,\ R^1(OC),\ LR^2N(R^3)SO_2Rf$$

3. The compound of claim 1, wherein $R^2$ comprises an alkylene of formula —(CyH2y)- where y is an integer in the range of 1 to 20.

4. The compound of claim 1, wherein $R^2$ comprises a combination of one or more alkylene groups and one or more arylene groups.

5. The compound of claim 4, wherein $R^2$ is a group of formula —($C_yH_{2y}$)—$Ar^1$—($C_yH_{2y}$)— where y is an integer in the range of 1 to 20 and $Ar^1$ is a phenylene or diphenylene.

6. The compound of claim 1, wherein the compound is $CH_3O(OC)$—[benzene ring]—$(CO)OCH_3$, $OCH_2CH_2N(CH_3)SO_2C_4F_9$ or $CH_3CH_2O(OC)$—[benzene ring]—$(CO)OCH_2CH_3$, $OCH_2CH_2N(CH_3)SO_2C_4F_9$, $C_4F_9SO_2N(CH_3)CH_2CH_2O$ 7. A fluorinated polyester comprising a condensation reaction product of a plurality of monomers comprising:
a) a compound of Formula (I)

$$(Rf—SO_2—N(R^3)—(R^2)_p—(L)_q)_n—Ar\begin{matrix}(CO)R^1\\(CO)R^1\end{matrix} \quad (I)$$

wherein
each $R^1$ is independently a halo, hydroxyl, alkoxy, or aryloxy, wherein the alkoxy is unsubstituted or substituted with an aryl and the aryloxy is unsubstituted or substituted with a halo, alkyl, or combination thereof;

Ar is an aromatic ring structure having at least 6 carbon atoms;

L is a single bond, oxy, thio, sulfonyl;

$R^2$ is a divalent group selected from an alkylene, heteroalkylene, arylene, or combination thereof;

$R^3$ is an alkyl;

Rf is a perfluoroalkyl, n is an integer in a range of 1 to 4;

p is an integer equal to 1;

q is an integer equal to 1; and b) a diol.

8. The fluorinated polyester of claim 7, wherein the compound of Formula (I) is a compound of Formula (Id) or (Ie)

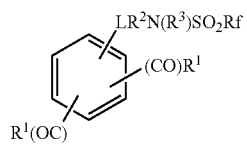
(Id)

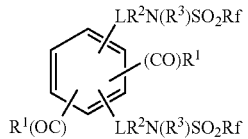
(Ie)

9. The fluorinated polyester of claim 7, wherein the diol is fluorinated.

10. The fluorinated polyester of claim 7, wherein the plurality of monomers further comprises a mono-functional end capping compound that is reactive with the compound of Formula (I) or with the diol.

* * * * *

UNITED STATES PATENT AND TRADEMARK OFFICE
CERTIFICATE OF CORRECTION

PATENT NO. : 8,686,179 B2
APPLICATION NO. : 13/322217
DATED : April 1, 2014
INVENTOR(S) : Yu Yang et al.

Page 1 of 2

It is certified that error appears in the above-identified patent and that said Letters Patent is hereby corrected as shown below:

In the Specification

Column 1
Line 63, delete "thereof" and insert -- thereof. --, therefor.

Column 3
Line 17, delete "thereof" and insert -- thereof. --, therefor.

Line 24, delete "thereof" and insert -- thereof. --, therefor.

Column 4
Line 35, delete "perfluoralkylsulfonamido" and insert -- perfluoroalkylsulfonamido --, therefor.

Column 7
Line 57 (Approx.), delete "Ij)." and insert -- (Ij). --, therefor.

Column 9
Line 53, delete "atom" and insert -- atoms and --, therefor.

Column 11
Line 4, delete "$R_4$" and insert -- $R^4$ --, therefor.

Column 14
Line 60, delete "c-$C_6F_{11}CH_2OH$," and insert -- $C_6F_{11}CH_2OH$, --, therefor.

Column 23
Lines 36-37, delete "perfluorbutanesulfonylethyl" and insert -- perfluorobutanesulfonylethyl --, therefor.

Line 53 (Approx.), delete "(poly-MeFBSEA)" and insert -- (poly-MeFBSEA). --, therefor.

Signed and Sealed this
Twelfth Day of August, 2014

Michelle K. Lee
*Deputy Director of the United States Patent and Trademark Office*

CERTIFICATE OF CORRECTION (continued)
U.S. Pat. No. 8,686,179 B2

In the Claims

Column 26
Line 12 (Approx.), In Claim 2, delete "(Ie)" and insert -- (Ie). --, therefor.

Line 30, In Claim 3, delete "(CyH2y)" and insert -- $(C_yH_{2y})$ --, therefor.

Column 27
Line 16, In Claim 8, delete "(Ie)" and insert -- (Ie). --, therefor.